(12) United States Patent
Catalucci et al.

(10) Patent No.: US 9,873,725 B2
(45) Date of Patent: Jan. 23, 2018

(54) MIMETIC PEPTIDES WHICH MODULATE L-TYPE CALCIUM CHANNELS

(71) Applicant: CONSIGLIO NAZIONALE DELLE RICERCHE, Rome (IT)

(72) Inventors: Daniele Catalucci, Segrate (IT); Gianluigi Condorelli, Rome (IT)

(73) Assignee: CONSIGLIO NAZIONALE DELLE RICERCHE, Rome (IT)

( * ) Notice: Subject to any disclaimer, the term of this patent is extended or adjusted under 35 U.S.C. 154(b) by 0 days.

(21) Appl. No.: 15/120,700

(22) PCT Filed: Jan. 23, 2015

(86) PCT No.: PCT/EP2015/051376
§ 371 (c)(1),
(2) Date: Aug. 22, 2016

(87) PCT Pub. No.: WO2015/110589
PCT Pub. Date: Jul. 30, 2015

(65) Prior Publication Data
US 2017/0008946 A1    Jan. 12, 2017

(30) Foreign Application Priority Data
Jan. 24, 2014   (IT) .............................. MI2014A0097

(51) Int. Cl.
| | | |
|---|---|---|
| C07K 14/705 | (2006.01) | |
| G01N 33/68 | (2006.01) | |
| G01N 33/50 | (2006.01) | |
| G06F 19/00 | (2011.01) | |
| A61K 38/00 | (2006.01) | |

(52) U.S. Cl.
CPC ....... *C07K 14/705* (2013.01); *G01N 33/5008* (2013.01); *G01N 33/6872* (2013.01); *G06F 19/70* (2013.01); *G06F 19/709* (2013.01); *A61K 38/00* (2013.01); *G01N 2333/705* (2013.01)

(58) Field of Classification Search
CPC ..... C07K 14/705; G06F 19/70; G06F 19/709; G01N 33/5008; G01N 33/6872; G01N 2333/705; A61K 38/00
See application file for complete search history.

(56) References Cited

U.S. PATENT DOCUMENTS

2002/0142938 A1    10/2002    Chunhua et al.

OTHER PUBLICATIONS

Smith RG, et al. N. Engl. J. Med. 327(24):1721-1728. Dec. 10, 1992. Available online at—DOI: 10.1056/NEJM199212103272405.*
Son MC and Brinton RD. Neurobiol. Learn Mem. 76(3):388-402. Nov 2001. Available online at—DOI: 10.1006/nlme.2001.4020.*
Barger SW. Neuroscience. 89(1):101-108. Mar. 1999. Available online at—https://doi.org/10.1016/S0306-4522(98)00312-1.*
Torborg C, et al. Vision Res. 44(28):3347-3355. Dec. 2004. Available online at—DOI:10.1016/j.visres.2004.08.015.*
Corrado et al., "Is It Time to Include Ion Channel Diseases Among Cardiomyopathies?" Journal of Electrocardiology, Elsevier Science 38(4):81-87 (2005).
Foell et al., "Molecular Heterogeneity of Calcium Channel β-subunits in Canine and Human Heart: Evidence for Differential Subcellular Localization," Physiological Genomics 17(2):183-200 (2004).
Harry et al., "New Short Splice Variants of the Human Cardiac Cavβ2 Subunit: Redefining the Major Functional Motifs Implemented in Modulation of the Cav1.2 Channel," Journal of Biological Chemistry 279(45):46367-46372 (2004).
Li et al., "Ion Channel Diseases of the Central Nervous System," CNS Drug Reviews 7(2):214-240 (2001).
Link et al., "Diversity and Developmental Expression of L-type Calcium Channel β2 Proteins and Their Influence on Calcium Current in Murine Heart," Journal of Biological Chemistry 284(44):30129-30137 (2009).
Database UniProt C7TQ54 (2009).
Database UniProt Q6TME0 (2004).
PCT International Search Report and Written Opinion corresponding to PCT/EP2015/051376 dated Apr. 28, 2015.
Catterall, W., "Voltage-Gated Calcium Channels," Cold Spring Harb Perspect Biol. 3(8):a003947 (2011).
Pasquale et al., "CaMKII Inhibition Rectifies Arrhythmic Phenotype in a Patient-specific Model of Catecholaminergic Polymorphic Ventricular Tachycardia," Cell Death Dis. 4:e843 (2013).
Catalucci et al., "Akt Regulates L-type Ca2+ Channel Activity by Modulating Cavalpha1 Protein Stability," J Cell Biol. 184(6):923-33 (2009).
Opatowsky et al., "Structural Analysis of the Voltage-dependent Calcium Channel Beta Subunit Functional Core and its Complex with the Alpha 1 Interaction Domain," Neuron. 42(3):387-99 (2004).

* cited by examiner

*Primary Examiner* — Robert Landsman
(74) *Attorney, Agent, or Firm* — LeClairRyan, a Professional Corporation

(57) ABSTRACT

The present invention concerns the field of ion channels, and in particular relates to peptides which are suitable for use in the treatment of conditions where the L-type calcium channel (LTCC) density and function is altered. LTCCs are located on the membrane of all excitable cells and control the small voltage gradient across the plasma membrane by allowing the flow of $Ca^{2+}$ ions down their electrochemical gradient. This $Ca^{2+}$ flux is critical for numerous processes including cardiac action potential propagation, muscle contraction, $Ca^{2+}$-dependent gene expression, synaptic efficacy, and cell survival by contributing to various signaling cascades. Reduction of the inward calcium current ($I_{Ca}$) conducted through the LTCCs is seen in several diseases and medications to improve or restores impaired intracellular $Ca^{2+}$ homeostasis are limited. The present invention reports mimetic peptides (MPs) that through a novel mechanism directly targets LTCCs and, by modulation of LTCC density and function, increases $I_{Ca}$. This invention supports a therapeutic role for MP to treat human diseases associated with altered cellular $Ca^{2+}$ homeostasis.

3 Claims, 9 Drawing Sheets

SEQUENCE LISTING

<160> NUMBER OF SEQ ID NOS: 26

<210> SEQ ID NO 1
<211> LENGTH: 7
<212> TYPE: PRT
<213> ORGANISM: Homo sapiens

```
<400> SEQUENCE: 1

Arg Pro Asp Arg Asp Ala Pro
1               5

<210> SEQ ID NO 2
<211> LENGTH: 7
<212> TYPE: PRT
<213> ORGANISM: Homo sapiens

<400> SEQUENCE: 2

Arg Pro Asp Arg Glu Ala Pro
1               5

<210> SEQ ID NO 3
<211> LENGTH: 11
<212> TYPE: PRT
<213> ORGANISM: Homo sapiens

<400> SEQUENCE: 3

Asp Gln Arg Pro Asp Arg Glu Ala Pro Arg Ser
1               5                   10

<210> SEQ ID NO 4
<211> LENGTH: 10
<212> TYPE: PRT
<213> ORGANISM: Homo sapiens

<400> SEQUENCE: 4

Asp Gln Arg Pro Asp Arg Glu Ala Pro Arg
1               5                   10

<210> SEQ ID NO 5
<211> LENGTH: 20
<212> TYPE: PRT
<213> ORGANISM: Homo sapiens

<400> SEQUENCE: 5

Asp Gln Arg Pro Asp Arg Glu Ala Pro Arg Ser Ala Ser Gln Ala Glu
1               5                   10                  15

Glu Glu Pro Cys
            20

<210> SEQ ID NO 6
<211> LENGTH: 26
<212> TYPE: PRT
<213> ORGANISM: Homo sapiens

<400> SEQUENCE: 6

Asp Gln Arg Pro Asp Arg Glu Ala Pro Arg Ser Ala Ser Gln Ala Glu
1               5                   10                  15

Glu Glu Pro Cys Leu Glu Pro Val Lys Lys
            20                  25

<210> SEQ ID NO 7
<211> LENGTH: 30
<212> TYPE: PRT
<213> ORGANISM: Homo sapiens

<400> SEQUENCE: 7

Asp Gln Arg Pro Asp Arg Glu Ala Pro Arg Ser Ala Ser Gln Ala Glu
1               5                   10                  15

Glu Glu Pro Cys Leu Glu Pro Val Lys Lys Ser Gln His Arg
```

<210> SEQ ID NO 8
<211> LENGTH: 10
<212> TYPE: PRT
<213> ORGANISM: Homo sapiens

<400> SEQUENCE: 8

```
Lys Gln Arg Asp Arg His Lys Glu Lys Asp
1               5                   10
```

<210> SEQ ID NO 9
<211> LENGTH: 10
<212> TYPE: PRT
<213> ORGANISM: Homo sapiens

<400> SEQUENCE: 9

```
Lys Gln Arg Asp Arg His Lys Asp Lys Asp
1               5                   10
```

<210> SEQ ID NO 10
<211> LENGTH: 34
<212> TYPE: PRT
<213> ORGANISM: Homo sapiens

<400> SEQUENCE: 10

```
Ile Ser Phe Glu Ala Lys Asp Phe Leu His Val Lys Glu Lys Phe Asn
1               5                   10                  15

Asn Asp Trp Trp Ile Gly Arg Leu Val Lys Glu Gly Cys Glu Ile Gly
            20                  25                  30

Phe Ile
```

<210> SEQ ID NO 11
<211> LENGTH: 11
<212> TYPE: PRT
<213> ORGANISM: Artificial
<220> FEATURE:
<223> OTHER INFORMATION: Scramble sequence

<400> SEQUENCE: 11

```
Asp Gln Pro Pro Ser Arg Arg Asp Glu Arg Ala
1               5                   10
```

<210> SEQ ID NO 12
<211> LENGTH: 23
<212> TYPE: PRT
<213> ORGANISM: Homo sapiens

<400> SEQUENCE: 12

```
Asp Gln Arg Pro Asp Arg Glu Ala Pro Arg Ser Ala Ser Gln Ala Glu
1               5                   10                  15

Glu Glu Pro Cys Leu Glu Pro
            20
```

<210> SEQ ID NO 13
<211> LENGTH: 14
<212> TYPE: PRT
<213> ORGANISM: Homo sapiens

<400> SEQUENCE: 13

```
Asp Gln Arg Pro Asp Arg Glu Ala Pro Arg Ser Ala Ser Gln
1               5                   10
```

```
<210> SEQ ID NO 14
<211> LENGTH: 11
<212> TYPE: PRT
<213> ORGANISM: Homo sapiens

<400> SEQUENCE: 14

Asp Gln Arg Pro Asp Arg Asp Ala Pro Arg Ser
1               5                   10

<210> SEQ ID NO 15
<211> LENGTH: 10
<212> TYPE: PRT
<213> ORGANISM: Homo sapiens

<400> SEQUENCE: 15

Asp Gln Arg Pro Asp Arg Asp Ala Pro Arg
1               5                   10

<210> SEQ ID NO 16
<211> LENGTH: 20
<212> TYPE: PRT
<213> ORGANISM: Homo sapiens

<400> SEQUENCE: 16

Asp Gln Arg Pro Asp Arg Asp Ala Pro Arg Ser Ala Ser Gln Ala Glu
1               5                   10                  15

Glu Glu Pro Cys
            20

<210> SEQ ID NO 17
<211> LENGTH: 26
<212> TYPE: PRT
<213> ORGANISM: Homo sapiens

<400> SEQUENCE: 17

Asp Gln Arg Pro Asp Arg Asp Ala Pro Arg Ser Ala Ser Gln Ala Glu
1               5                   10                  15

Glu Glu Pro Cys Leu Glu Pro Val Lys Lys
            20                  25

<210> SEQ ID NO 18
<211> LENGTH: 30
<212> TYPE: PRT
<213> ORGANISM: Homo sapiens

<400> SEQUENCE: 18

Asp Gln Arg Pro Asp Arg Asp Ala Pro Arg Ser Ala Ser Gln Ala Glu
1               5                   10                  15

Glu Glu Pro Cys Leu Glu Pro Val Lys Lys Ser Gln His Arg
            20                  25                  30

<210> SEQ ID NO 19
<211> LENGTH: 23
<212> TYPE: PRT
<213> ORGANISM: Homo sapiens

<400> SEQUENCE: 19

Asp Gln Arg Pro Asp Arg Asp Ala Pro Arg Ser Ala Ser Gln Ala Glu
1               5                   10                  15

Glu Glu Pro Cys Leu Glu Pro
            20

<210> SEQ ID NO 20
```

```
<211> LENGTH: 14
<212> TYPE: PRT
<213> ORGANISM: Homo sapiens

<400> SEQUENCE: 20

Asp Gln Arg Pro Asp Arg Asp Ala Pro Arg Ser Ala Ser Gln
1               5                   10

<210> SEQ ID NO 21
<211> LENGTH: 10
<212> TYPE: PRT
<213> ORGANISM: Homo sapiens

<400> SEQUENCE: 21

Lys Gln Arg Ser Arg His Lys Glu Lys Asp
1               5                   10

<210> SEQ ID NO 22
<211> LENGTH: 10
<212> TYPE: PRT
<213> ORGANISM: Homo sapiens

<400> SEQUENCE: 22

Lys Gln Arg Ser Arg His Lys Asp Lys Asp
1               5                   10

<210> SEQ ID NO 23
<211> LENGTH: 9
<212> TYPE: PRT
<213> ORGANISM: Homo sapiens

<400> SEQUENCE: 23

Arg Ser Gln Ala Glu Glu Glu Pro Cys
1               5

<210> SEQ ID NO 24
<211> LENGTH: 15
<212> TYPE: PRT
<213> ORGANISM: Homo sapiens

<400> SEQUENCE: 24

Arg Ser Gln Ala Glu Glu Glu Pro Cys Leu Glu Pro Val Lys Lys
1               5                   10                  15

<210> SEQ ID NO 25
<211> LENGTH: 19
<212> TYPE: PRT
<213> ORGANISM: Homo sapiens

<400> SEQUENCE: 25

Arg Ser Gln Ala Glu Glu Glu Pro Cys Leu Glu Pro Val Lys Lys Ser
1               5                   10                  15

Gln His Arg

<210> SEQ ID NO 26
<211> LENGTH: 12
<212> TYPE: PRT
<213> ORGANISM: Homo sapiens

<400> SEQUENCE: 26

Arg Ser Gln Ala Glu Glu Glu Pro Cys Leu Glu Pro
1               5                   10
```

MIMETIC PEPTIDES WHICH MODULATE L-TYPE CALCIUM CHANNELS

This application is a national stage application under 35 U.S.C. §371 of PCT Application No. PCT/EP2015/051376, filed Jan. 23, 2015, which claims the priority benefit of Italian Patent Application No. MI2014A000097, filed Jan. 24, 2014.

FIELD OF THE INVENTION

The present invention concerns the field of ion channels, and in particular relates to peptides which are suitable for use in the treatment of conditions where the L-type calcium channel density is altered.

STATE OF THE ART

Ion channels are integral membrane proteins that help establish and control the small voltage gradient across the plasma membrane of living cells by allowing the flow of ions down their electrochemical gradient. They are present in the membranes that surround all biological cells regulating the flow of ions across it.

L-Type Calcium Channels (LTCCs) are ion channels that couple membrane depolarization to cellular $Ca^{2+}$ entry[1]. LTCCs are critical for numerous processes including cardiac action potential propagation, muscle contraction, $Ca^{2+}$-dependent gene expression, synaptic efficacy, and cell survival by contributing to various signaling cascades. LTCCs play a critical role in $Ca^{2+}$ dependent signaling processes in a variety of cell types and are mostly found in skeletal muscle, smooth muscle, bone (osteoblasts), atrial and ventricular myocytes (responsible for prolonged action potential in cardiac cell; also termed DHP receptors), dendrites and dendritic spines of cortical neurons. In particular LTCCs can be found in excitable cells such as cardiac and skeletal muscles, smooth muscles, neuronal cells, cells which are present in the eye and are responsible for vision.

LTCCs are the initiators of the $Ca^{2+}$-induced $Ca^{2+}$ release (CICR) process in the heart and are composed of different subunits: the pore-forming subunit $Ca_v\alpha1.2$ and the accessory $Ca_v\beta2$ and $Ca_v\alpha2\delta$ subunits. The number of functional LTCCs at the plasma membrane strongly influences the strength and duration of $Ca^{2+}$ signals triggering myocardial systolic/diastolic cycles and cardiac rhythm and changes in the LTCC density have been observed in aging and various diseases.

Indeed, a trend for the $Ca^{2+}$ channel density to decline has been found with the progression of pathological hypertrophy, dilated cardiomyopathy, atrial/ventricular fibrillation, and diabetic cardiomyopathy. In addition, recent evidence has revealed that loss-of-function mutations in genes coding for subunits of the LTCC, once considered rare, are now recognized as relatively common and to be associated with a wide variety of inherited cardiac arrhythmic syndromes, including Timothy, early repolarization, short QT syndrome and Brugada syndromes. Thus, these observations highlight the pivotal role of LTCCs in health and disease and support the view that LTCCs may represent a reasonable pharmacologic target for the treatment of variety of pathological conditions that need novel therapeutic approaches to reduce their morbidity and mortality.

In the past few years major advancements have been made in the understanding of the abnormalities of $Ca^{2+}$ regulation present in human diseases and efforts are being made to turn this knowledge into novel therapeutic strategies targeting $Ca^{2+}$-related ion exchangers, binding proteins and ion-channels to prevent or reverse $Ca^{2+}$ handling dysfunction.

Exhaustive understandings of the molecular mechanisms underlying LTCC structural and functional alterations occurring in cardiac pathologies as well as in other LTCC-related (or $Ca^{2+}$-dependent) pathologies in general, are required.

The need and importance is increasingly felt for the development of small molecules such as therapeutic peptides for the treatment of conditions having altered LTCC functionality, which are more target-specific and avoid adverse effects of currently available drugs.

It is therefore object of the present invention the development of novel mimetic peptides as innovative tools, which allow to modulate the quantity of intracellular $Ca^{2+}$ available for activating excitable cells (i.e. for binding and activating muscle contractile proteins).

SUMMARY OF THE INVENTION

The present invention concerns an isolated peptide comprising the amino acid sequence of SEQ ID NO:10, and its use as a peptide binding domain. The amino acid sequence set forth in SEQ ID NO:10 corresponds to a previously unknown binding domain [hereafter referred to as Tail Interacting Domain (TID), see Example 1] of the $Ca_v\beta2$ target protein, which is the binding site of the peptides (set forth in SEQ ID NO:1 to 9 and SEQ ID NO:12 to 22) and which, upon binding to the TID, extend the half-life of the $Ca_v\alpha1.2$ protein, pore-forming subunit of LTCCs. This modulation of LTCC density restores the intracellular $Ca^{2+}$ handling in conditions where alterations of $Ca^{2+}$ homeostasis in excitable cells determine the extent and severity of the disease.

The invention also relates to mimetic peptides set forth in SEQ ID NO:1 to 9 and SEQ ID NO:12 to 22 that bind to the peptide binding domain TID of the $Ca_v\beta2$ protein according to SEQ ID NO:10, thus acting on the modulation of the density and function of LTCCs.

As will be further described in the detailed description of the invention, the present invention concerns an isolated peptide having an amino acid sequence chosen from the group consisting of:

```
                                      (SEQ ID NO: 2)
A-Arg-Pro-Asp-Arg-Glu-Ala-Pro-B
or
                                      (SEQ ID NO: 1)
A-Arg-Pro-Asp-Arg-Asp-Ala-Pro-B
or
                                      (SEQ ID NO: 8)
Lys-Gln-Arg-Asp-Arg-His-Lys-Glu-Lys-Asp,
or,
                                      (SEQ ID NO: 9)
Lys-Gln-Arg-Asp-Arg-His-Lys-Asp-Lys-Asp;
or
                                     (SEQ ID NO: 21)
Lys-Gln-Arg-Ser-Arg-His-Lys-Glu-Lys-Asp,
or
                                      (SEQ ID NO 22)
Lys-Gln-Arg-Ser-Arg-His-Lys-Asp-Lys-Asp,
``` wherein:
A is an amino acid sequence which is optionally present, and if present is chosen from the group consisting of Asp-Gln-, and B is an amino acid sequence which is optionally present, and if present is chosen from the group consisting of: Arg-, Arg-Ser, Arg-Ser-Gln-Ala-Glu-Glu-Glu-Pro-Cys (SEQ ID NO:23), Arg-Ser-Gln-Ala-Glu-Glu-Glu-Pro-Cys-Leu-Glu-Pro-Val-Lys-Lys (SEQ ID NO:24), Arg-Ser-Gln-Ala-Glu-Glu-Glu-Pro-Cys-Leu-Glu-Pro-Val-Lys-Lys-Ser-Gln-His-Arg (SEQ ID NO:25), Arg-Ser-Gln, or Arg-Ser-Gln-Ala-Glu-Glu-Glu-Pro-Cys-Leu-Glu-Pro (SEQ ID NO:26).

The peptides of the present invention have the advantages of being specific for LTCCs as they bind to a pocket domain (TID, SEQ ID NO:10) in the $Ca_v\beta2$ protein, subunit of the LTCC.

A further aspect of the present invention is the use of an isolated peptide chosen from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 for the preparation of a medicament.

In a still further aspect the invention relates to the use of an isolated peptide chosen from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 for the treatment of conditions having altered LTCC density and function.

A further aspect of the present invention relates to a pharmaceutical composition comprising one or more peptides chosen from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and/or pharmaceutically acceptable carrier.

A further aspect of the present invention relates to the use of the isolated peptide chosen from the SEQ ID NO:10 for further optimization and development of novel peptides (in addition to SEQ ID NO:1-9 and SEQ ID NO:12-22) or synthetic compounds able to bind the TID binding domain in $Ca_v\beta2$ and to modulate LTCC density and function.

BRIEF DESCRIPTION OF THE DRAWINGS

The characteristics and advantages of the present invention will be apparent from the detailed description reported below, from the Examples given for illustrative and non-limiting purposes, and from the annexed FIGS. 1-9, wherein.

DETAILED DESCRIPTION OF THE INVENTION

Figure 1:
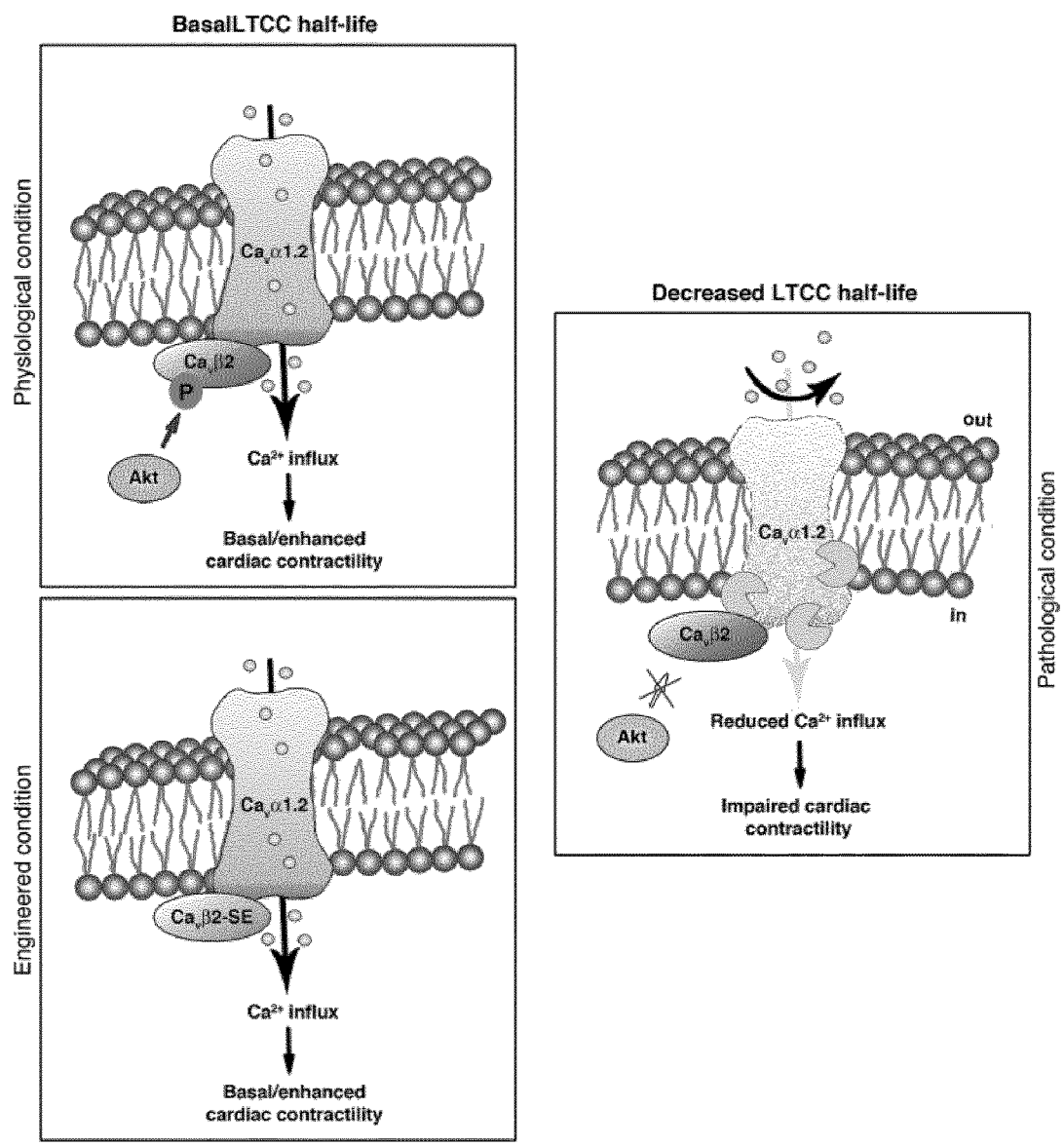
FIG. 1: shows schematic working model of modulation of LTCC half-life in basal (top left), engineered (bottom left), and pathological (right) conditions.

The present invention concerns an isolated peptide comprising the amino acid sequence of SEQ ID NO:10, corresponding to the TID binding domain of the Ca$_v$β2 target protein.

Ca$_v$β2 is the Voltage-dependent L-type calcium channel subunit beta-2, also known as CACNB2 [gene ID 783 (*Homo sapiens*), gene ID 12296 (*Mus musculus*)].

The TID binding site of the Ca$_v$β2 (SEQ ID NO:10) was previously unknown and it has been here revealed as a triggering domain for the modulation of Ca$_v$α1.2 protein half-life. In particular, peptides binding to the TID induce a molecular mechanism that increases Ca$_v$α1.2 protein density and function at the plasma membrane.

The importance of identifying the exact binding site of the Ca$_v$β2, (SEQ ID NO:10 Ile-Ser-Phe-Glu-Ala-Lys-Asp-Phe-Leu-His-Val-Lys-Glu-Lys-Phe-Asn-Asn-Asp-Trp-Trp-Ile-Gly-Arg-Leu-Val-Lys-Glu-Gly-Cys-Gludle-Gly-Phe-Ile) and in particular the amino acids (highlighted in bold in SEQ ID NO:10 Ile-Ser-Phe-Glu-Ala-Lys-Asp-Phe-Leu-His-Val-Lys-Glu-Lys-Phe-Asn-Asn-Asp-Trp-Trp-Ile-Gly-Arg-Leu-Val-Lys-Glu-Gly-Cys-Gludle-Gly-Phe-Ile (SEQ ID NO:10) and further described in example 1) which are responsible for the direct ionic bond between the TID in Ca$_v$β2 and the activator peptides (SEQ ID NO: 1 to 9 and SEQ ID NO: 12 to 22) is widely recognized and allowed the identification of mimetic peptides which modulate the channel's density and activity.

In a further aspect the invention relates to the use of the isolated peptide of SEQ ID NO:10 as a peptide binding domain. In particular, this peptide-binding domain in Ca$_v$β2 is relevant for further optimization and development of novel mimetic peptides or synthetic compounds that are more specific for the binding to the TID domain in Ca$_v$β2 and lead to a modulation of LTCC density and function. In a further aspect the invention concerns mimetic peptides (SEQ ID NO: 1 to 9 and SEQ ID NO:12 to 22) that bind to the TID peptide binding domain of the Ca$_v$β2 protein according to SEQ ID NO:10, thus acting on density and function of voltage dependent LTCCs.

In a preferred aspect the invention concerns an isolated peptide having an amino acid sequence chosen from the group consisting of:

```
                                                (SEQ ID NO: 2)
A-Arg-Pro-Asp-Arg-Glu-Ala-Pro-B
or (SEQ ID NO: 1)
A-Arg-Pro-Asp-Arg-Asp-Ala-Pro-B
or (SEQ ID NO: 8)
Lys-Gln-Arg-Asp-Arg-His-Lys-Glu-Lys-Asp,
or, (SEQ ID NO: 9)
Lys-Gln-Arg-Asp-Arg-His-Lys-Asp-Lys-Asp;
or (SEQ ID NO: 21)
Lys-Gln-Arg-Ser-Arg-His-Lys-Glu-Lys-Asp,
or (SEQ ID NO: 22)
Lys-Gln-Arg-Ser-Arg-His-Lys-Asp-Lys-Asp,
``` wherein:

A is an amino acid sequence which is optionally present, and if present is chosen from the group consisting of Asp-Gln-, and B is an amino acid sequence which is optionally present, and if present is chosen from the group consisting of: Arg-, Arg-Ser, Arg-Ser-Gln-Ala-Glu-Glu-Glu-Pro-Cys (SEQ ID NO:23), Arg-Ser-Gln-Ala-Glu-Glu-Glu-Pro-Cys-Leu-Glu-Pro-Val-Lys-Lys (SEQ ID NO:24), Arg-Ser-Gln-Ala-Glu-Glu-Glu-Pro-Cys-Leu-Glu-Pro-Val-Lys-Lys-Ser-Gln-His-Arg (SEQ ID NO:25), Arg-Ser-Gln, or Arg-Ser-Gln-Ala-Glu-Glu-Glu-Pro-Cys-Leu-Glu-Pro (SEQ ID NO:26).

TABLE 1

| Peptide number | SEQ ID NO. | peptide amino acid sequence (three letter code) | peptide amino acid sequence (one letter code) |
|---|---|---|---|
| 1 | SEQ ID NO: 1 | Arg-Pro-Asp-Arg-Asp-Ala-Pro | RPDRDAP |
| 2 | SEQ ID NO: 2 | Arg-Pro-Asp-Arg-Glu-Ala-Pro | RPDREAP |
| 3 | SEQ ID NO: 3 | Asp-Gln-Arg-Pro-Asp-Arg-Glu-Ala-Pro-Arg-Ser | DQRPDREAPRS |
| 4 | SEQ ID NO: 4 | Asp-Gln-Arg-Pro-Asp-Arg-Glu-Ala-Pro-Arg | DQRPDREAPR |

TABLE 1-continued

| Peptide number | SEQ ID NO. | peptide amino acid sequence (three letter code) | peptide amino acid sequence (one letter code) |
|---|---|---|---|
| 5 | SEQ ID NO: 5 | Asp-Gln-Arg-Pro-Asp-Arg-Glu-Ala-Pro-Arg-Ser-Ala-Ser-Gln-Ala-Glu-Glu-Glu-Pro-Cys | DQRPDREAPRSASQAEEEPC |
| 6 | SEQ ID NO: 6 | Asp-Gln-Arg-Pro-Asp-Arg-Glu-Ala-Pro-Arg-Ser-Ala-Ser-Gln-Ala-Glu-Glu-Glu-Pro-Cys-Leu-Glu-Pro-Val-Lys-Lys | DQRPDREAPRSASQAEEEPCLEPVKK |
| 7 | SEQ ID NO: 7 | Asp-Gln-Arg-Pro-Asp-Arg-Glu-Ala-Pro-Arg-Ser-Ala-Ser-Gln-Ala-Glu-Glu-Glu-Pro-Cys-Leu-Glu-Pro-Val-Lys-Lys-Ser-Gln-His-Arg | DQRPDREAPRSASQAEEEPCLEPVKKSQHR |
| 8 | SEQ ID NO: 8 | Lys-Gln-Arg-Asp-Arg-His-Lys-Glu-Lys-Asp | KQRDRHKEKD |
| 9 | SEQ ID NO: 9 | Lys-Gln-Arg-Asp-Arg-His-Lys-Asp-Lys-Asp | KQRDRHKDKD |
| 10 | SEQ ID NO: 10 | Ile-Ser-Phe-Glu-Ala-Lys-Asp-Phe-Leu-His-Val-Lys-Glu-Lys-Phe-Asn-Asn-Asp-Trp-Trp-Ile-Gly-Arg-Leu-Val-Lys-Glu-Gly-Cys-Glu-Ile-Gly-Phe-Ile | ISFEAKDFLHVKEKFNNDWWIGRLVKEGCEIGFI |
| 11 | SEQ ID NO: 11 | Asp-Gln-Pro-Pro-Ser-Arg-Arg-Asp-Glu-Arg-Ala | DQPPSRRDERA |
| 12 | SEQ ID NO: 12 | Asp-Gln-Arg-Pro-Asp-Arg-Glu-Ala-Pro-Arg-Ser-Ala-Ser-Gln-Ala-Glu-Glu-Glu-Pro-Cys-Leu-Glu-Pro | DQRPDREAPRSASQAEEEPCLEP |
| 13 | SEQ ID NO: 13 | Asp-Gln-Arg-Pro-Asp-Arg-Glu-Ala-Pro-Arg-Ser-Ala-Ser-Gln | DQRPDREAPRSASQ |
| 14 | SEQ ID NO: 14 | Asp-Gln-Arg-Pro-Asp-Arg-Asp-Ala-Pro-Arg-Ser | DQRPDRDAPRS |
| 15 | SEQ ID NO: 15 | Asp-Gln-Arg-Pro-Asp-Arg-Asp-Ala-Pro-Arg | DQRPDRDAPR |
| 16 | SEQ ID NO: 16 | Asp-Gln-Arg-Pro-Asp-Arg-Asp-Ala-Pro-Arg-Ser-Ala-Ser-Gln-Ala-Glu-Glu-Glu-Pro-Cys | DQRPDRDAPRSASQAEEEPC |
| 17 | SEQ ID NO: 17 | Asp-Gln-Arg-Pro-Asp-Arg-Asp-Ala-Pro-Arg-Ser-Ala-Ser-Gln-Ala-Glu-Glu-Glu-Pro-Cys-Leu-Glu-Pro-Val-Lys-Lys | DQRPDRDAPRSASQAEEEPCLEPVKK |
| 18 | SEQ ID NO: 18 | Asp-Gln-Arg-Pro-Asp-Arg-Asp-Ala-Pro-Arg-Ser-Ala-Ser-Gln-Ala-Glu-Glu-Glu-Pro-Cys-Leu-Glu-Pro-Val-Lys-Lys-Ser-Gln-His-Arg | DQRPDRDAPRSASQAEEEPCLEPVKKSQHR |
| 19 | SEQ ID NO: 19 | Asp-Gln-Arg-Pro-Asp-Arg-Asp-Ala-Pro-Arg-Ser-Ala-Ser-Gln-Ala-Glu-Glu-Glu-Pro-Cys-Leu-Glu-Pro | DQRPDRDAPRSASQAEEEPCLEP |
| 20 | SEQ ID NO: 20 | Asp-Gln-Arg-Pro-Asp-Arg-Asp-Ala-Pro-Arg-Ser-Ala-Ser-Gln | DQRPDRDAPRSASQ |
| 21 | SEQ ID NO: 21 | Lys-Gln-Arg-Ser-Arg-His-Lys-Glu-Lys-Asp | KQRSRHKEKD |
| 22 | SEQ ID NO: 22 | Lys-Gln-Arg-Ser-Arg-His-Lys-Asp-Lys-Asp | KQRSRHKDKD |
| 23 | SEQ ID NO: 23 | Arg-Ser-Gln-Ala-Glu-Glu-Glu-Pro-Cys | RSQAEEEPC |

TABLE 1-continued

| Peptide number | SEQ ID NO. | peptide amino acid sequence (three letter code) | peptide amino acid sequence (one letter code) |
|---|---|---|---|
| 24 | SEQ ID NO: 24 | Arg-Ser-Gln-Ala-Glu-Glu-Glu-Pro-Cys-Leu-Glu-Pro-Val-Lys-Lys | RSQAEEEPCLEPVKK |
| 25 | SEQ ID NO: 25 | Arg-Ser-Gln-Ala-Glu-Glu-Glu-Pro-Cys-Leu-Glu-Pro-Val-Lys-Lys-Ser-Gln-His-Arg | RSQAEEEPCLEPVKKSQHR |
| 26 | SEQ ID NO: 26 | Arg-Ser-Gln-Ala-Glu-Glu-Glu-Pro-Cys-Leu-Glu-Pro | RSQAEEEPCLEP |

For the purposes of the present invention, each isolated peptide has a corresponding SEQ ID NO., according to the following Table 1.

The isolated peptides of the present invention have the amino acid sequences defined in Table 1, in which the three and one letter IUPAC amino acid code is used (ie. Arg and R corresponds to the amino acid Arginine, Pro and P corresponds to the amino acid Proline). Each peptide has a peptide number and a corresponding SEQ ID NO., as above reported in the Table 1.

The subject of the invention is therefore a novel group of low molecular weight peptides, which can be chemically synthesized.

These peptides are of synthetic origin and are therefore easy to manufacture in large quantities, and they can be modified chemically and biologically or conjugates to other moieties (i.e. carriers).

These peptides have the advantages of being of synthetic origin, and therefore do not have the disadvantages seen in natural peptides such as the tendency to induce inflammatory response and pathogen transfer due to undefined factors that cannot be eliminated by purification prior to implantation, the significant degree of variability between different lots and the difficulty of availability of large scale sources.

When compared with proteins/antibodies or even small organic molecules, the peptides according to the present invention offer advantages such as: i) good biocompatibility; ii) reduced side effects due to limited systemic toxicity or drug—drug interactions (e.g. degradation products are amino acids); iii) reduced secondary complications (e.g. minor tissue accumulation) due to a relatively short half-life of peptides (or their metabolites); (in addition, proteolysis can be prevented by chemical modifications); iv) generally less immunogenicity; v) potentially more penetrating into tissues due to smaller size; vi) good efficacy, selectivity and specificity and limited off-target binding; vii) ease of chemical synthesis and modification, free of impurities and side products; viii) low manufacturing costs.

In addition, since the therapeutic peptide-binding site in the protein target is known and set forth in SEQ ID NO:10, this allows for further drug optimization (i.e. drug design for increased selectivity).

In a further aspect, the invention regards an isolated peptide, wherein:

(SEQ ID NO: 2)
A-Arg-Pro-Asp-Arg-Glu-Ala-Pro-B
or (SEQ ID NO: 1)
A-Arg-Pro-Asp-Arg-Asp-Ala-Pro-B or (SEQ ID NO: 8)
Lys-Gln-Arg-Asp-Arg-His-Lys-Glu-Lys-Asp,
or, (SEQ ID NO: 9)
Lys-Gln-Arg-Asp-Arg-His-Lys-Asp-Lys-Asp;
or (SEQ ID NO: 21)
Lys-Gln-Arg-Ser-Arg-His-Lys-Glu-Lys-Asp,
or (SEQ ID NO: 22)
Lys-Gln-Arg-Ser-Arg-His-Lys-Asp-Lys-Asp, wherein:
A is an amino acid sequence which is optionally present, and if present is chosen from the group consisting of Asp-Gln-, and
B is an amino acid sequence which is optionally present, and if present is chosen from the group consisting of: Arg-, Arg-Ser, Arg-Ser-Gln-Ala-Glu-Glu-Glu-Pro-Cys (SEQ ID NO:23), Arg-Ser-Gln-Ala-Glu-Glu-Glu-Pro-Cys-Leu-Glu-Pro-Val-Lys-Lys (SEQ ID NO:24), Arg-Ser-Gln-Ala-Glu-Glu-Glu-Pro-Cys-Leu-Glu-Pro-Val-Lys-Lys-Ser-Gln-His-Arg (SEQ ID NO:25), Arg-Ser-Gln, or Arg-Ser-Gln-Ala-Glu-Glu-Glu-Pro-Cys-Leu-Glu-Pro (SEQ ID NO:26).

In a preferred aspect, the invention relates to an isolated peptide according to the invention, chosen from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22.

In a further aspect the invention relates to the use of an isolated peptide chosen from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 for the preparation of a medicament.

The peptides of the present invention surprisingly have been shown to be useful in the preparation of a medicament (Examples 4, 5, 6, and 7).

In a still further embodiment the invention relates to the use of an isolated peptide chosen from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 for the treatment of conditions having altered LTCC density (Examples 4, 5, 6, and 7)

In general, peptides of the invention may be useful in any situation involving conditions having altered LTCC density or in those conditions where an intervention for the modulation of LTCC density or intracellular $Ca^{2+}$ concentration is preferable. Such conditions may occur as a result of genetic and/or metabolic disorders, and/or other diseases and/or conditions.

Peptides of the invention aim at augmenting LTCC protein density by extending the calcium channel half-life through a mechanism that rely on the binding of peptides to a solvent-exposed domain (TID, SEQ ID NO:10) in $Ca_v\beta2$ protein, subunit of LTCC.

Certain peptides of the present invention may be used to ameliorate the effects of diseases such as heart pathology.

In a preferred aspect the invention relates to the use of an isolated peptide chosen from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 wherein said conditions having altered LTCC density and function are cardiovascular dysfunctions selected from the group consisting of heart failure, reduction of myocardial contraction, fibrillation, diabetic cardiomyopathy, dilated cardiomyopathy, genetic-based disorders (i.e. channelopathies such as Brugada syndrome, Timothy syndrome, or short QT syndrome), cardiac hypertrophy, hypotension, hyperthyroidism, hypothyroidism, acute heart failure, chronic heart failure, myocardial infarction.

In a still further aspect the invention relates to the use of an isolated peptide chosen from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21 wherein said conditions having altered LTCC density and function are ophthalmological conditions selected from the group consisting of lens transparency, and altered intraocular pressure.

In a still further aspect the invention relates to the use of an isolated peptide chosen from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 wherein said conditions having altered LTCC density and function are neurological conditions selected from the group consisting of vascular dementia, Alzheimer's disease, Parkinson's disease, Prion disease and hypokalemic periodic paralysis.

In a further aspect, the invention relates to a pharmaceutical composition comprising one or more peptides chosen from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and/or pharmaceutically acceptable carrier.

Exemplary pharmaceutically acceptable carriers or excipients include any and all solvents, dispersion media, diluents, or other liquid vehicles, dispersion or suspension aids, surface active agents, isotonic agents, thickening or emulsifying agents, preservatives, solid binders, lubricants and the like, nanoparticles, nucleic acids (i.e aptamers), cell-penetrating molecules or peptides as suited to the particular form of administration and dosage.

The pharmaceutical composition according to the present invention can be for enteral and parenteral administration (i.e. intravenous, intraperitoneal, oral, sublingual, aerosol, inhalation, spray, rectal, intraocular, topical or transdermal).

In another aspect the invention relates to method of screening for a peptide or other synthetic molecule which binds the amino acid sequence of SEQ ID NO:10 comprising the steps of:

a) transfecting a mammalian cell with a nucleic acid construct comprising SEQ ID NO:10;
b) contacting said mammalian cell with a screening compound;
c) detecting the binding of the screening compound to the mammalian cell;

or d) virtual high throughput screening of compound library database to identify peptides or molecules of novel chemical structure that bind to the $Ca_v\beta2$ macromolecular target comprising SEQ ID NO:10;

or e) computer-aided drug design of compounds that bind to the $Ca_v\beta2$ macromolecular target comprising SEQ ID NO:10.

In a still further embodiment the invention relates to peptides or synthetic molecules which are identified and obtained in the method of screening wherein said peptide or synthetic molecule binds the amino acid sequence of SEQ ID NO:10 in the method described above in the present invention.

In particular, the invention relates to a peptide or synthetic molecule which binds the amino acid sequence of SEQ ID NO:10 obtainable according to the method of screening comprising the steps of:

a) transfecting a mammalian cell with a nucleic acid construct comprising SEQ ID NO:10;
b) contacting said mammalian cell with a screening compound;
c) detecting the binding of the screening compound to the mammalian cell;

or d) virtual high throughput screening of compound library database to identify peptides or molecules of novel chemical structure that bind to the $Ca_v\beta2$ macromolecular target comprising SEQ ID NO:10;

or e) computer-aided drug design of compounds that bind to the $Ca_v\beta2$ macromolecular target comprising SEQ ID NO:10.

Use of the peptide or synthetic molecule which binds the amino acid sequence of SEQ ID NO:10 for the treatment of conditions having altered LTCC density and function, said peptide or synthetic molecule obtainable according to the method of screening comprising the steps of:

a) transfecting a mammalian cell with a nucleic acid construct comprising SEQ ID NO:10;
b) contacting said mammalian cell with a screening compound;
c) detecting the binding of the screening compound to the mammalian cell;

or d) virtual high throughput screening of compound library database to identify peptides or molecules of novel chemical structure that bind to the $Ca_v\beta2$ macromolecular target comprising SEQ ID NO:10;
or
e) computer-aided drug design of compounds that bind to the $Ca_v\beta2$ macromolecular target comprising SEQ ID NO:10.

EXAMPLES

Results below were partially funded by Fondazione Cariplo (grant n° 2008.2504)

Example 1

Identification of a Previously Unknown Binding Domain in $Ca_v\beta2$ (TID; SEQ ID NO:10)

Figure 2:
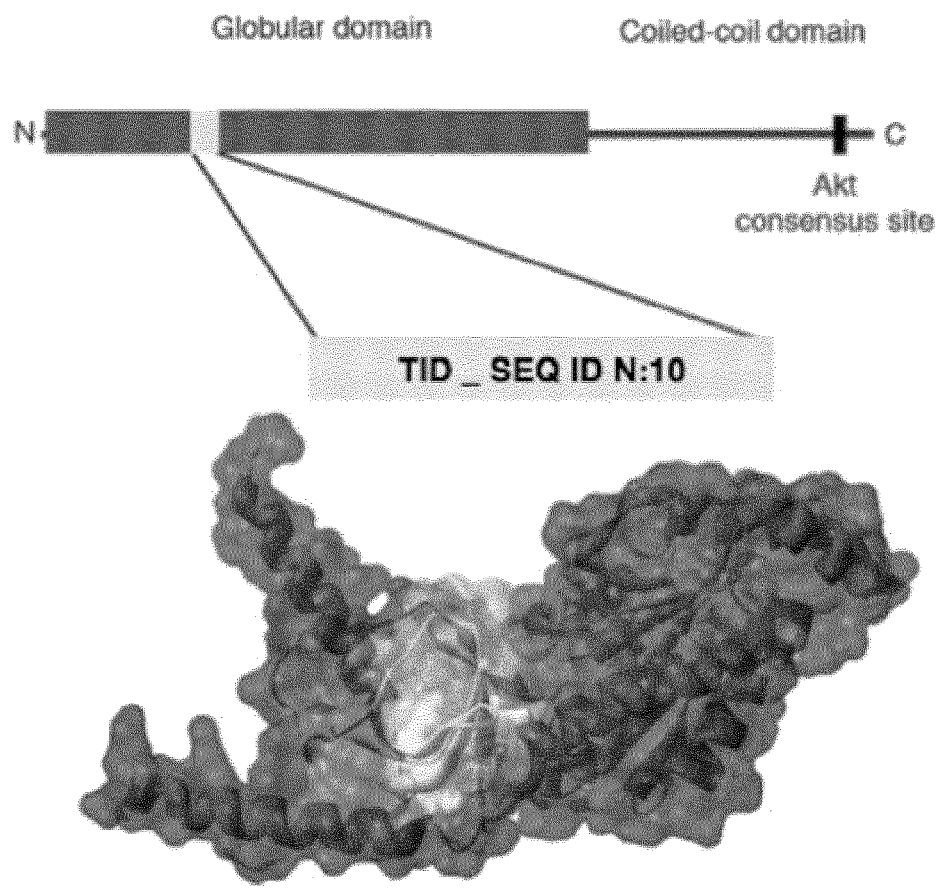
FIG. 2: shows identification of a previously unknown binding domain in $Ca_v\beta2$ (TID; SEQ ID NO:10) as described in Example 1. (a, top) schematic representation of $Ca_v\beta2$ [dark grey box (globular domain); dark grey line (coiled-coil); light grey box (TID); black (Akt consensus site)]. (a, bottom) 3D structure of $Ca_v\beta2$ ($Ca_v\beta2$ PDB code: 1T3S[2]) where solvent accessibility of the TID for a potential protein-protein interaction is shown in light grey; (b) Yeast two-hybrid co-transformation: b-galactosidase activity (dark grey) in streaks of yeast cells on a culture plate, Hu=human, Ms=*mus musculus*; labels show the bait and/or prey plasmids transformed into the yeast cells; and (c) co-immunoprecipitation assay of identified positive clones. HEK293 and tSA-201 cells were transfected as indicated (n=4).
Figure 2:
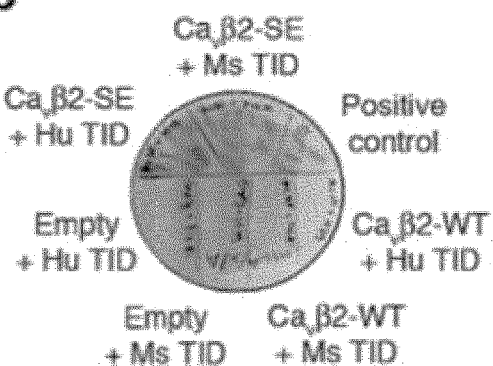
Figure 2:
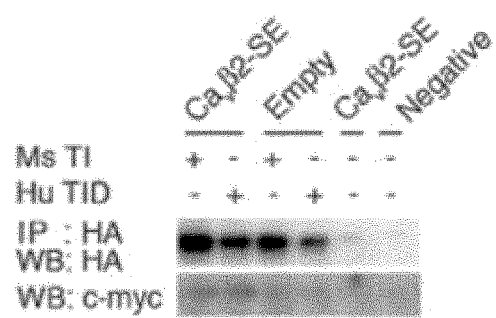

Our previous in vitro findings showed that an Akt-dependent phosphorylation of $Ca_v\beta2$, either directly through the kinase or by introduction of an Akt-phosphomimetic mutation (Ser to Glu, $Ca_v\beta2$-SE) in the Akt consensus-site of $Ca_v\beta2$ cDNA, was sufficient to enhance the $Ca_v\alpha1.2$(and thus LTCC) half-life and thus intracellular $Ca^{2+}$ handlings and cardiomyocyte contractility (FIG. 1)[3]. Based on this evidence, we designed experiments to determine the sequence of structural and molecular events that link Akt-mediated phosphorylation of $Ca_v\beta2$ to the inhibition of $Ca_v\alpha1.2$ degradation. As a first step, we investigated whether upon Akt-phosphorylation, $Ca_v\beta2$ recruits additional interacting partners to inhibit $Ca_v\alpha1.2$ degradation. We performed a yeast-two-hybrid screening using Akt-phosphomimetic $Ca_v\beta2$ cDNA ($Ca_v\beta2$-SE) as a bait and either human or mouse heart cDNA expression libraries as preys. Remarkably, several positive clones corresponded to $Ca_v\beta2$ in a region belonging to the globular domain (FIG. 2a,b), whereas no $Ca_v\beta2$ clones were found when the assay was repeated with a wildtype $Ca_v\beta2$-WT bait. Co-immuno-precipitation analyses of lysates obtained from HEK293 cells co-transfected with the $Ca_v\beta2$-SE bait and either mouse or human $Ca_v\beta2$-prey clones confirmed the specificity of the interaction (FIG. 2c).

Finally, when amino acid sequences from the identified positive clones were aligned (FIG. 2a, top) and analyzed for solvent accessibility (FIG. 2a, bottom), we identified a minimal common region potentially binding to the $Ca_v\beta2$ C-terminal region, which we named Tail Interacting Domain (TID; SEQ ID NO:10).

Figure 3:
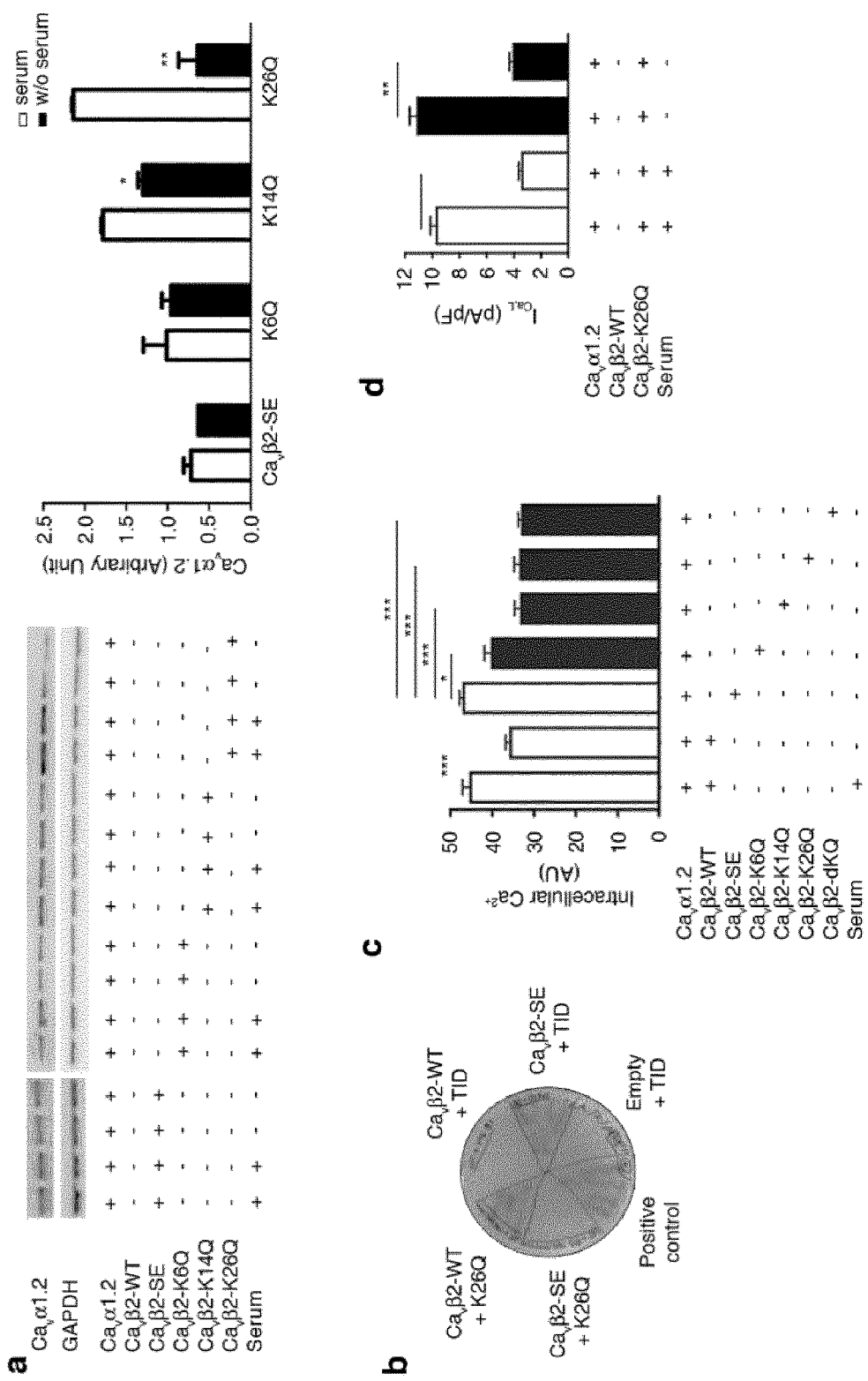
FIG. 3: shows the effects of site-specific mutagenesis in the TID binding site and $Ca_v\alpha1.2$ stability as described in Example 1. a) Western blotting analysis (left) and densitometry measurements (right) of $Ca_v\alpha1.2$ and GAPDH protein levels of total protein lysates from HEK293 transfected cells; b) Yeast two-hybrid co-trasformation: b-galactosidase activity (dark grey) in streaks of yeast cells on a culture plate; labels show the bait and/or prey plasmids transformed into the yeast cells; (c) $Ca^{2+}$ flux analysis from HEK293 transfected cells; (d) $Ca^{2+}$ current measurements in tSA-201 transfected cells. HEK293 and tSA-201 cells were transfected as indicated. $Ca_v\alpha1.2$ protein degradation was elicited in vitro with cell starvation (serum removal). Protein levels were normalized to GAPDH. (n=4). Data are shown as the means±SEM; *, P<0.05, , P<0.005; *, P<0.001.

To assess whether TID plays a direct role in the molecular mechanism that protects $Ca_v\alpha1.2$ from protein degradation, we used site-specific mutagenesis forreplacing positively charged Lysines (K) at positions 6, 14, and 26 in the TID (SEQ ID NO:10) sequence with Glutamines (Q) to destroy any potential ionic interaction between the binding domain and the coiled-coil. Whereas co-transfection of HEK293 cells with $Ca_v\alpha1.2$ and $Ca_v\beta2$-SE resulted in unaltered $Ca_v\alpha1.2$ protein levels when Akt was not activated (i.e. upon serum removal), the introduction of the K26Q site mutation in TID strongly impaired the protective effect (FIG. 3a, right panel). Similar results, but to a different extent, were obtained when the other amino acids in the TID were mutated (FIG. 3a, right panel). A yeast two-hybrid assay with $Ca_v\beta2$-SE as a bait and the K26Q mutated $Ca_v\beta2$ as a prey showed no interaction, confirming the direct role of K26 in SEQ ID NO:10 for the interaction (FIG. 3b). Subsequently, a fluorescence-based $Ca^{2+}$ assay was used to analyze LTCC-mediated intracellular $Ca^{2+}$ flux. Co-transfection of $Ca_v\alpha1.2$ with any of the mutated $Ca_v\beta2$-SE constructs resulted in a significant reduction in $Ca^{2+}$ flux upon serum removal, down to a level that was similar to the one of the control condition (FIG. 3c). In addition, $I_{Ca}$ measurements showed a significant reduction in current when tSA-201 cells were transfected with $Ca_v\beta2$-SE-K26Q compared to $Ca_v\beta2$-SE (FIG. 3d).

Example 2

Mimetic Peptides (MPs) Affect LTCC Protein Stability and Function In Vitro

Based on the evidence shown in example 1, we next investigated whether mimetic peptides (MPs) might recapitulate the mechanism by which LTCCs are protected from protein degradation by binding to the TID domain. Thus, we transfected HEK293 cells with an array of partially overlapping peptides (length from 7 to 25 amino acids) belonging to the $Ca_v\beta2$ terminal coiled-coil region and subsequently performed Western blot (FIG. 4a) and intracellular $Ca^{2+}$ measurements (FIG. 4b), identifying several peptides that, to different extents, were efficient in protecting LTCC protein stability and function upon serum removal. No evidence for significant apoptosis was found (FIG. 4a).

Figure 4:
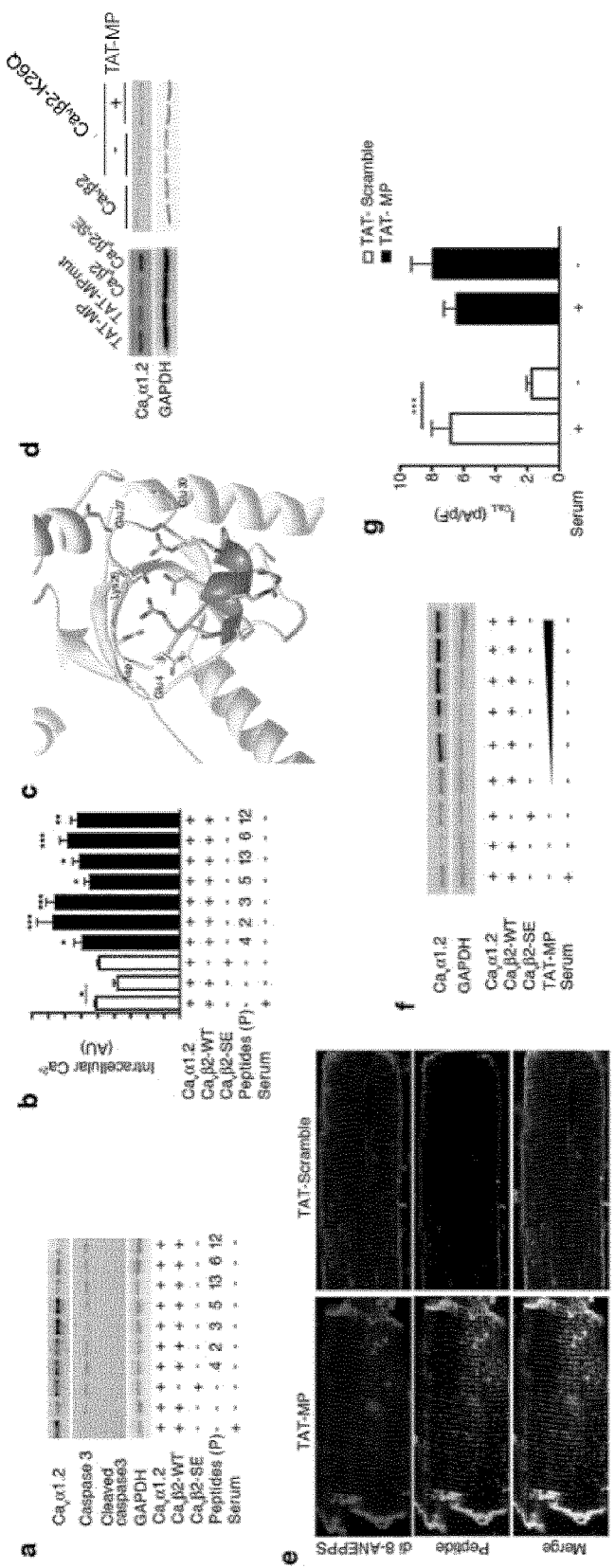
FIG. 4: shows the effects of peptides on $Ca_v\alpha1.2$ protein stability and function as described in Example 2 and 3.
a) Western blotting analysis of $Ca_v\alpha1.2$ and GAPDH protein levels of total protein lysates; b) Intracellular $Ca^{2+}$ fluxes; (c) Molecular modeling and docking of a peptide (SEQ ID NO:2, dark grey) to TID region (SEQ ID NO:10, light grey) of $Ca_v\beta2$.; (d) Western blotting analysis of $Ca_v\alpha1.2$ and GAPDH protein levels of total protein lysates; (e) Confocal analyses of adult cardiomyocytes treated with TAT-MP- and TAT-scramble-and stained with di 8-ANEPPS dye. MP=SEQ ID NO:3, scramble=SEQ ID NO:11. (f) Western blotting analysis of $Ca_v\alpha1.2$ and GAPDH protein levels of total protein lysates from HEK293 cells treated with increasing doses of MP; (g) $Ca^{2+}$ current measurements in tSA-201 cells previously transfected. For Western blotting analyses, HEK293 or tSA-201 cells transfected or treated as indicated. Protein levels were normalized to GAPDH. (n=4). Data are shown as the means±SEM; *, P<0.05, , P<0.005; *, P<0.001. Peptides are chosen from the group listed in Table 1.
Figure 5:
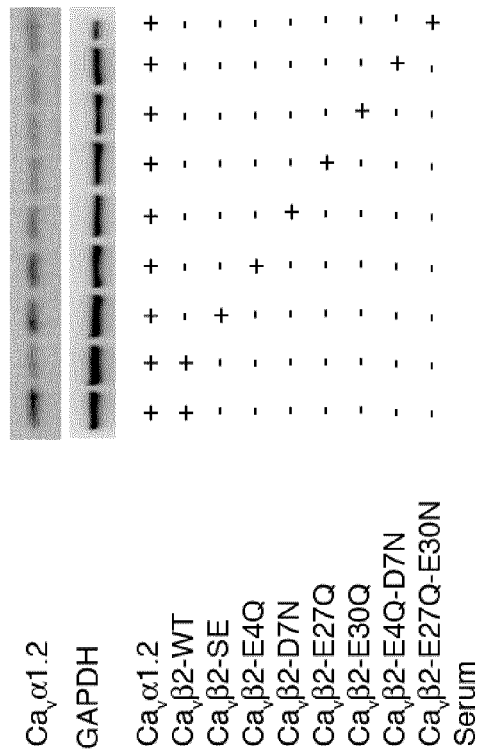
FIG. 5: shows the effects of site-specific mutagenesis in the TID binding site and $Ca_v\alpha1.2$ stability as described in Example 2. Western blotting analysis of $Ca_v\alpha1.2$ and GAPDH protein levels of total protein lysates from HEK293 transfected cells. $Ca_v\alpha1.2$ protein degradation was elicited in vitro with cell starvation (serum removal). HEK293 cells were transfected as indicated. Protein levels were normalized to GAPDH. (n=4).

By computational docking simulation, we tested the ability of the identified MPs to recognize the TID region and predicted that MP most specifically recognize the TID region by direct interaction with the lysine residue K26 and formation of electrostatic interactions between two arginine residues and negatively charged regions of the functional core of the $Ca_v\beta2$ (FIG. 4c). In line with this, additional site-directed mutagenesis analyses in $Ca_v\beta2$ further supported this prediction and found E4, D7, E27, and E30 in SEQ ID NO:10 relevant for the binding MP-TID (FIG. 5). The specificity of the selected MP (SEQ ID NO: 3) was subsequently confirmed in vitro as the protective effect of the selected MP on $Ca_v\alpha1.2$ was completely lost when specific mutations within either the MP or $Ca_v\alpha1.2$ abolished the predicted interaction between MP and TID (FIG. 4d).

Example 3

Modified MP Penetrates the Plasma Membrane and Affect LTCC Function In Vitro

To facilitate the intracellular uptake, a cell-penetrating peptide (CPP) was conjugated to the MP (SEQ ID NO: 3). To overcome any potential steric hindrance that a CPP might have when fused to the MP, we evaluated our $Ca_v\beta2$-MP 3D model (FIG. 4d) and predicted the N-terminus of MP as a suitable region for CCP fusion. Thus, the trans-activating transcriptional activator (TAT) from Human Immunodeficiency Virus 1 (HIV-1) was used. When administered to isolated cardiomyocytes, this cell-penetrating derivative of the MP peptide (TAT-MP) was shown to specifically co-localize with LTCCs (FIG. 4e), protect $Ca_v\alpha1.2$ from protein degradation (FIG. 4f), and preserve $Ca^{2+}$ current (FIG. 4g) upon serum removal. On the other hand, none of these effects were observed when a scramble peptide was used. TAT-MP=SEQ ID NO: 3; TAT-scramble=scramble=SEQ ID NO:11.

Example 4

Therapeutic Potential of Mimetic Peptides (Genetic Mouse Model of Heart Failure)

Figure 6:
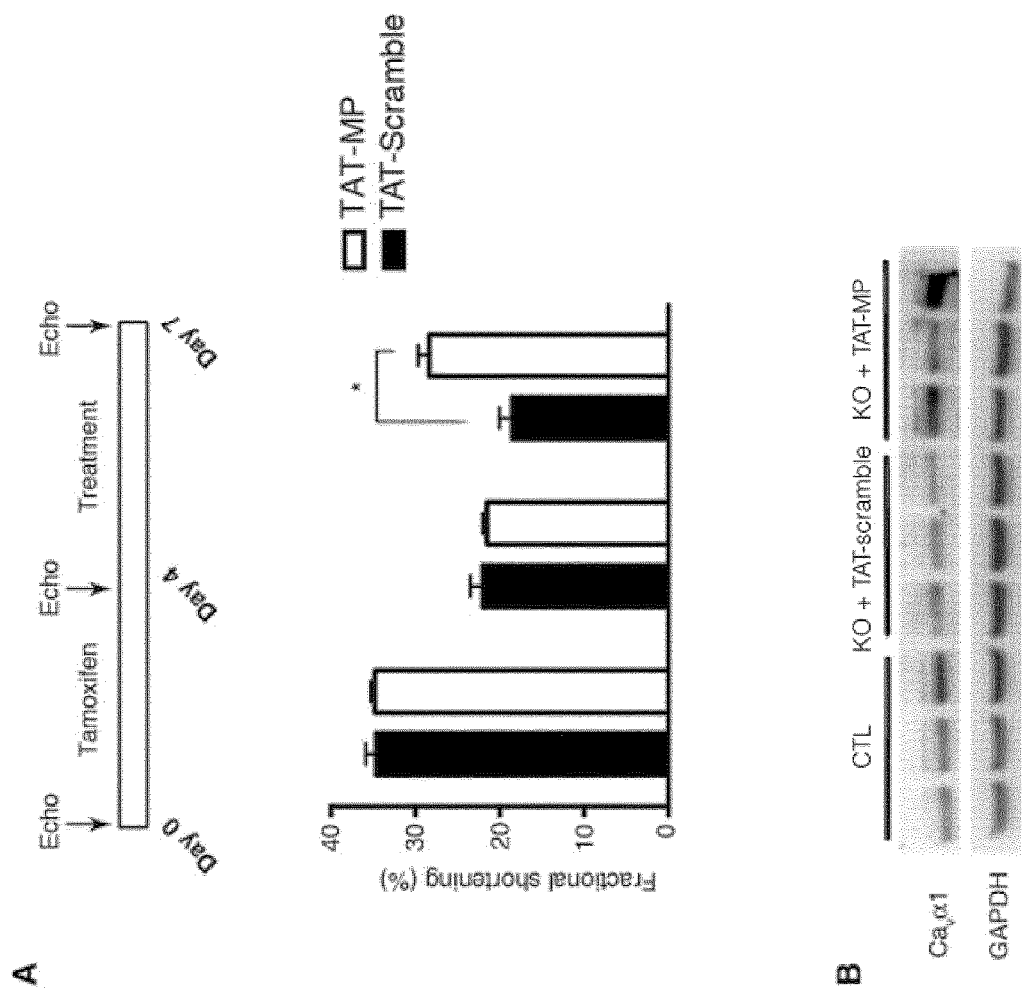
FIG. 6: shows the therapeutic potential of mimetic peptide in a genetic mouse model of heart failure as described in Example 4. (a, top) Design of study. Echo, echocardiography. (a, bottom) Fractional shortening (%) as determined by echocardiography in pdk1 knockout mice treated with mimetic peptide (TAT-MP) or scramble (TAT-scramble). (b) Western blotting analysis of $Ca_v\alpha1.2$ and GAPDH protein levels of total protein lysates from left ventricular homogenates. Protein levels were normalized to GAPDH. (n=4) MP=SEQ ID NO:3, scramble=SEQ ID NO:11. Tamoxifen (TAM) and peptide was injected daily as indicated. Protein levels were normalized to GAPDH. Data are shown as the means±SEM; *, P<0.05.

To explore the in vivo therapeutic potential, MP was used in an inducible and cardiac specific knockout of the phosphoinositide-dependent kinase 1 (PDK1), the upstream activator of all three Akt isoforms. As previously reported[3], deletion of PDK1 by tamoxifen injection resulted with a reduction of cardiac function as evaluated by echocardiographic analysis. We then treated the mice with either cell penetrating MP or scramble peptides and followed the phenotype for the following days. Whereas animals treated with scrambles displayed progressive impairment of left ventricular function, animals treated with MP showed significant attenuation of the impairment of cardiac function that corresponded to a restoration of LTCC protein levels (FIG. 6). MP=SEQ ID NO: 3; TAT-scramble=scramble=SEQ ID NO:11.

Example 5

Therapeutic Potential of Mimetic Peptides (Diabetic Cardiomyopathy)

Figure 7:
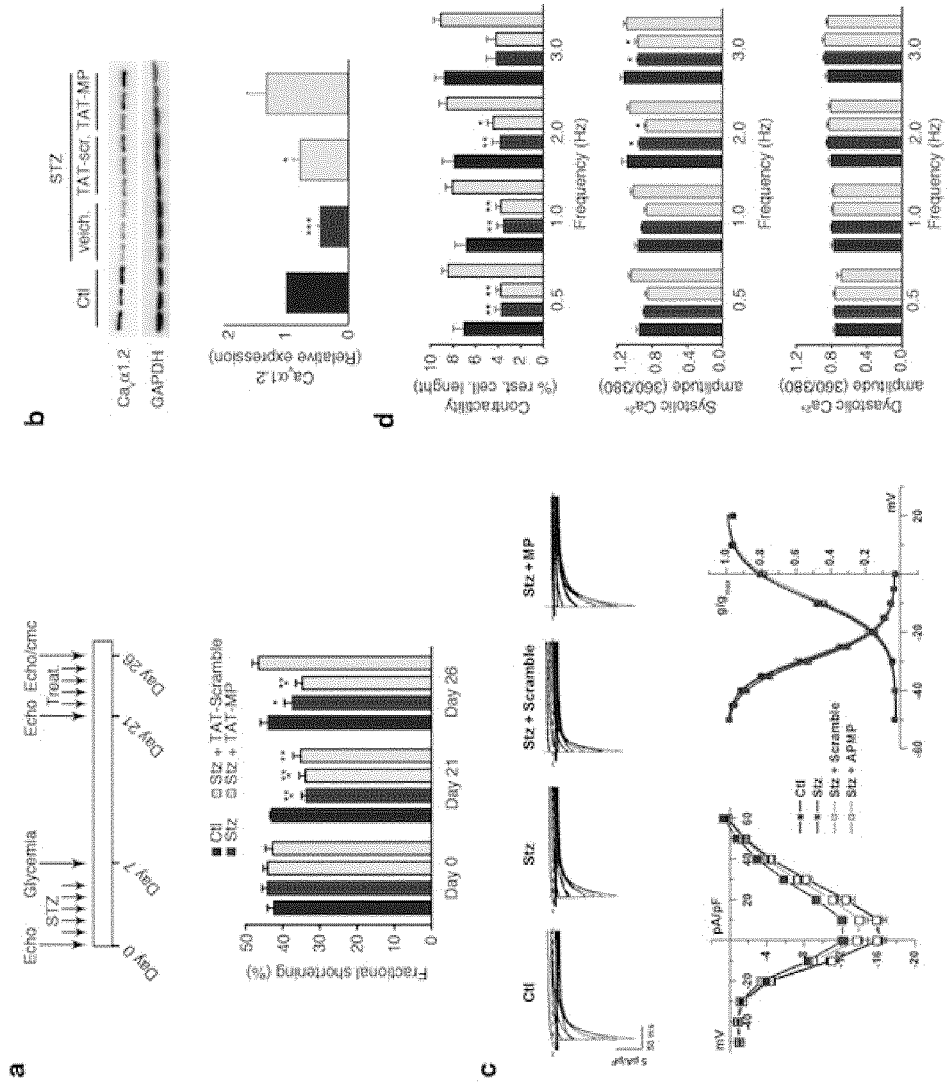
FIG. 7: shows the therapeutic potential of mimetic peptide in a mouse model of diabetic cardiomyopathy. (a, top) Design of study. Echo, echocardiography. (a, bottom) Fractional shortening (%) as determined by echocardiography in mice treated with streptozotocin (STZ) and mimetic peptide (TAT-MP) or scramble (TAT-scramble). (n=10) (b) Western blotting analysis and densitometry of $Ca_v\alpha1.2$ and GAPDH protein levels of total protein lysates from left ventricular homogenates. (c) Ca²⁺ current measurements in cardiomyocytes isolated from treated mice. (d, top) contractility and (d, middle and bottom) systolic and diastolic Ca²⁺ transient measurements in cardiomyocytes isolated from treated mice. Cardiomyocytes were analyzed at different pacing (Hz). MP=SEQ ID NO:3, scramble=SEQ ID NO:11. Protein levels were normalized to GAPDH. STZ and peptide were injected daily as indicated. Data are shown as the means±SEM; *, P<0.05, , P<0.005; *, P<0.001.

To further explore the potential therapeutic application, we assessed the effects of the TAT-MP in a mouse model of cardiomyopathy in which LTCC density, and consequently cardiac contractility, is downregulated (i.e. diabetic cardiomyopathy, DM). Alterations in $Ca^{2+}$ signaling within cardiac muscle cells are a hallmark of DM. The defects identified in the mechanical activity of hearts from diabetic animals are attributed to a reduction in Ica, a decrease in systolic $Ca^{2+}$, and a lengthening of the systolic $Ca^{2+}$ transient, primarily resulting from dysfunction of the SR. To induce DM, mice were injected with streptozotocin (STZ), a compound that is toxic for the insulin-producing beta cells of the pancreas (FIG. 7). In line with the effects of the insulin/Akt signaling on LTCCs, cardiac dysfunction in DM mice was associated with reduced Caval 0.2 protein levels in DM mice compared to control mice (FIG. 7b). Intriguingly, 4 days of treatment of DM mice with TAT-MP (MP=SEQ ID NO: 3) nearly completely restored cardiac function (FIG. 7a), while no effects were obtained when vehicle or TAT-scramble (scramble=SEQ ID NO:11) where administered. In addition, functional analyses of cardiomyocytes isolated from the same treated mice revealed that the TAT-MP restored $I_{Ca}$ as well as cell contractility and systolic $Ca^{2+}$ amplitudes (FIG. 7c,d).

Example 6

Therapeutic Potential of Mimetic Peptides (Human Cardiac Model)

To pursue the cardiac therapeutic potential of MP, we employed a human cardiac model that is based on cardiomyocytes (CMs) differentiated from induced pluripotent stem cells (iPSCs) and previously derived from skin fibroblasts of healthy individuals[4]. iPSC-CMs subjected to an Akt inhibitor showed a downregulation of $Ca_v\alpha1.2$ protein levels that was prevented when cells were co-treated with MP (MP=SEQ ID NO: 3) (FIG. 8a). On the other hand, no rescuing effects were obtained when scramble peptide was used. Based on this, we next performed functional analyses and examined the iPSC-CM beating clusters (BCs) for $Ca^{2+}$ handling properties. While administration of Akt-inhibitor to BCs showed a significant slowing of $Ca^{2+}$ transient development, indicating an alteration between LTCC activity and evoked $Ca^{2+}$ release from the sarcoplasmatic reticulum, MP administration was sufficient for reducing this delay (FIG. 8b,c). On the other hand, no effects were observed when BCs were co-treated with scramble.

Example 7

Therapeutic Potential of Mimetic Peptides (Inherited Cardiac Arrhythmic Disease, i.e Brugada Syndrome)

Figure 8:
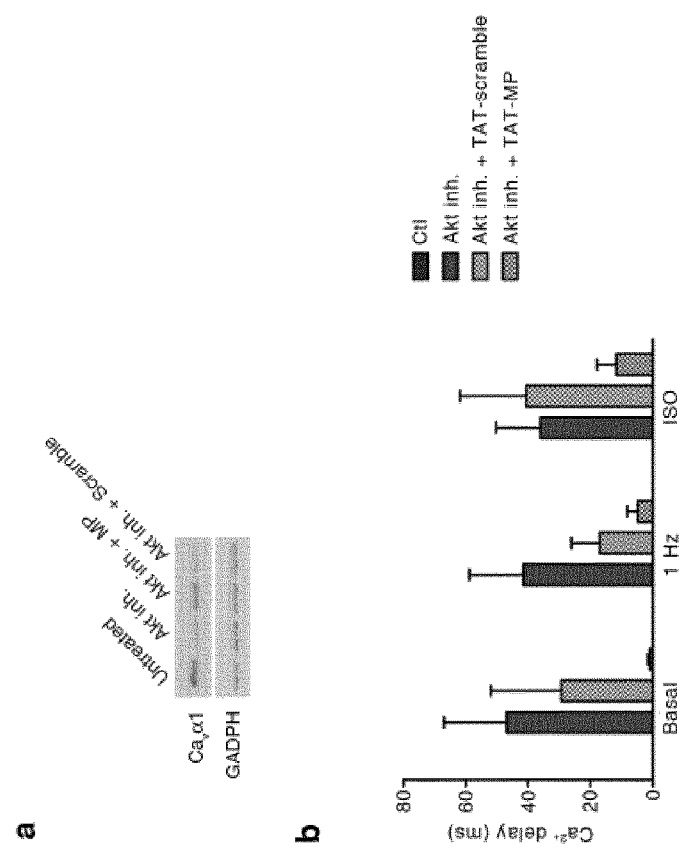
FIG. 8: shows the therapeutic potential of mimetic peptide in a human cardiac model as described in Example 6. (a) Western blotting analysis of Ca$_v$α1.2 and GAPDH protein levels of total protein lysates from cardiomyocytes (CMs) differentiated from induced pluripotent stem cells (iPSCs) and previously derived from skin fibroblasts of healthy individuals. (n=4) Cells were untreated or treated with an Akt-inhibitor. MP=SEQ ID NO:3, scramble=SEQ ID NO:11.
Figure 9:
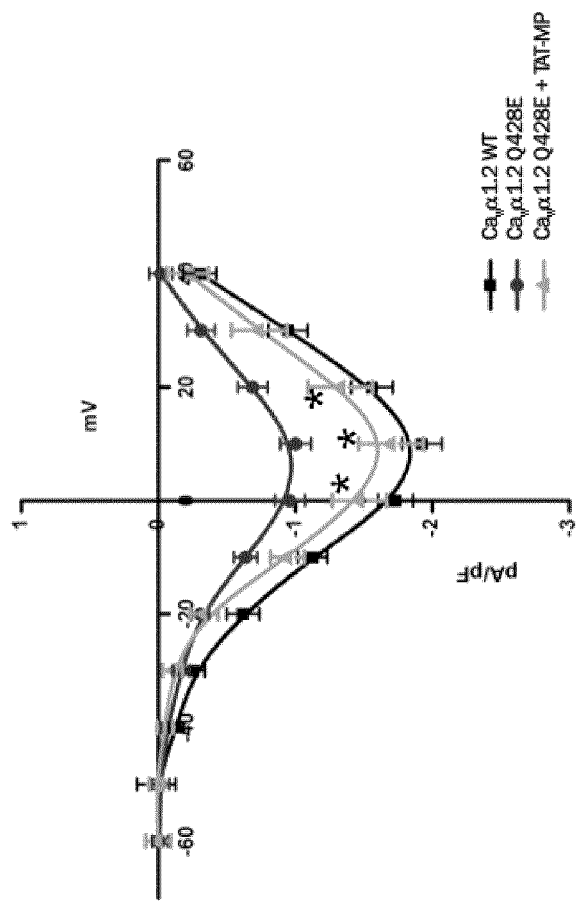
FIG. 9: shows the therapeutic potential of mimetic peptide in a model of inherited cardiac arrhythmic syndrome (Brugada) as described in Example 6. $I_{Ca}$ current density was normalized for cell capacitance. The Ca$_v$α1.2 mutation occurs within the Q420E site. HEK293 cells were transfected as indicated. MP=SEQ ID NO:3 (n=15 cells/group). * p<0.05 vs. baseline for MP groups.

To test whether the potential therapeutic use of the TAT-MP (MP=SEQ ID NO:3) may also exert a corrective effect in conditions of patients are affected by Brugada Syndrome (BrS) and who are carriers of loss of function mutations in the CACNA1C gene encoding for the $Ca_v\alpha1.2$ subunit of the LTCC. BrS is an inherited arrhythmogenic disease estimated to account for 20% of sudden deaths in young patients with an otherwise normal hearts. Thus, we investigated whether the loss of function in the LTCC caused by missense mutations (i.e the substitution of Glutamine at position 428 with a Glutamic Acid found in a patient diagnosed after a cardiac arrest at 32 years of age occurring at rest) in the CACNA1C gene identified in BrS patients could be reverted by the administration of TAT-MP. Membrane currents were measured using whole-cell patch clamp procedures to obtain the current-voltage (I-V) relationship. The current-voltage (I-V) relationships between WT and Q428E showed that amplitudes of current were significantly reduced as compared to WT (FIG. 8). Treatment of cells expressing mutant $Ca_v\alpha1.2$ with TAT-MP nearly completely reverted the loss-of-current phenotype induced by the $Ca_v\alpha1.2$ mutation.

From the above description and the above-noted examples, the advantage attained by the product described and obtained according to the present invention are apparent.

REFERENCES

1 Catterall, W. A. Voltage-gated calcium channels. *Cold Spring Harbor perspectives in biology* 3, a003947, doi: 10.1101/cshperspect.a003947 (2011).
2 Opatowsky, Y., Chen, C. C., Campbell, K. P. & Hirsch, J. A. Structural analysis of the voltage-dependent calcium channel beta subunit functional core and its complex with the alpha 1 interaction domain. *Neuron* 42, 387-399 (2004).
3 Catalucci, D. et al. Akt regulates L-type Ca2+ channel activity by modulating Cavalphal protein stability. *The Journal of cell biology* 184, 923-933, doi:10.1083/jcb.200805063 (2009).
4 Di Pasquale, E. et al. CaMKII inhibition rectifies arrhythmic phenotype in a patient-specific model of catecholaminergic polymorphic ventricular tachycardia. *Cell death & disease* 4, e843, doi:10.1038/cddis.2013.369 (2013).

The invention claimed is:

1. An isolated peptide, said isolated peptide having an amino acid sequence chosen from the group consisting of:

A-Arg-Pro-Asp-Arg-Glu-Ala-Pro-B  (SEQ ID NO: 2)

or

A-Arg-Pro-Asp-Arg-Asp-Ala-Pro-B  (SEQ ID NO: 1)

wherein:

A is an amino acid sequence which is optionally present, and if present is chosen from the group consisting of Asp-Gln-, and B is an amino acid sequence which is optionally present, and if present is chosen from the group consisting of: Arg-, Arg-Ser, Arg-Ser-Gln-Ala-Glu-Glu-Glu-Pro-Cys (SEQ ID NO:23), Arg-Ser-Gln-Ala-Glu-Glu-Glu-Pro-Cys-Leu-Glu-Pro-Val-Lys-Lys (SEQ ID NO:24), Arg-Ser-Gln-Ala-Glu-Glu-Glu-Pro-Cys-Leu-Glu-Pro-Val-Lys-Lys-Ser-Gln-His-Arg (SEQ ID NO:25), Arg-Ser-Gln, or Arg-Ser-Gln-Ala-Glu-Glu-Glu-Pro-Cys-Leu-Glu-Pro (SEQ ID NO:26).

2. The isolated peptide according to claim 1, chosen from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20.

3. A pharmaceutical composition comprising one or more peptides chosen from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20 and/or pharmaceutically acceptable carrier, for enteral and parenteral administration, by intravenous, intraperitoneal, oral, sublingual, aerosol, inhalation, spray, rectal, intraocular, topical or transdermal.

* * * * *